United States Patent [19]

Lockhart

[11] Patent Number: 4,471,769
[45] Date of Patent: Sep. 18, 1984

[54] SURGICAL DRAPE

[75] Inventor: Frank D. Lockhart, Columbus, Miss.

[73] Assignee: Teknamed Corporation, Columbus, Miss.

[21] Appl. No.: 338,181

[22] Filed: Jan. 8, 1982

[51] Int. Cl.$^3$ ............................................. A61F 13/00
[52] U.S. Cl. .............................. 128/132 D; 2/DIG. 7
[58] Field of Search ....................... 2/51, DIG. 7, 114; 604/355–357; 128/132 D, 155, 157

[56] References Cited

U.S. PATENT DOCUMENTS

| | | | |
|---|---|---|---|
| 2,593,121 | 4/1952 | Djorup | 604/357 |
| 3,494,356 | 2/1970 | Melqes | 128/132 D |
| 3,693,618 | 9/1972 | Madden | 128/132 D |
| 3,741,206 | 6/1973 | Binard et al. | 128/132 D |
| 3,799,161 | 3/1974 | Collins | 128/132 D |
| 3,862,632 | 1/1975 | Hinsch | 128/132 D |
| 4,007,741 | 2/1977 | Waldrop et al. | 604/357 |
| 4,027,665 | 6/1977 | Scrivens | 128/132 D |
| 4,378,794 | 4/1983 | Collins | 128/132 D |

Primary Examiner—C. Fred Rosenbaum
Assistant Examiner—J. L. Kruter
Attorney, Agent, or Firm—Beveridge, DeGrandi and Kline

[57] ABSTRACT

A surgical drape has a main sheet for draping over a patient's torso, a pair of leg flaps for draping over the patient's legs, and a liquid impervious sheet which has an opening for providing access to the patient.

The leg flaps are connected to the main sheet and they extend laterally inwardly. Their forward and distal edges are movable so they may cover the legs of either a reclining patient whose knees are straight or a reclining patient whose knees are raised and bent in a lithotomy position.

The liquid impervious sheet has its forward end connected to the main sheet. It has a second opening which provides a second access to the patient and a drain opening which permits the drainage of liquid. Removable liquid impervious coverings are provided over the latter two openings. To prevent liquid from flowing over the sides of the impervious sheet, its margins are provided with adhesive areas which are used to form tucks in the sheet. The length of the impervious sheet is such that it may be attached to the torso of the physician by pressure sensitive tapes which are provided at the rear end of the sheet.

33 Claims, 6 Drawing Figures

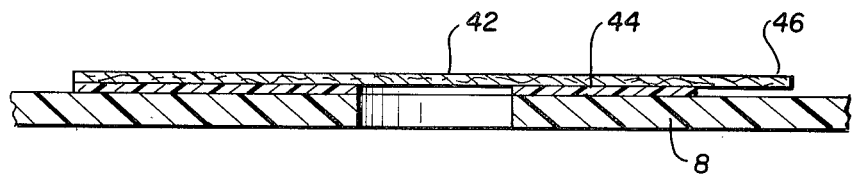
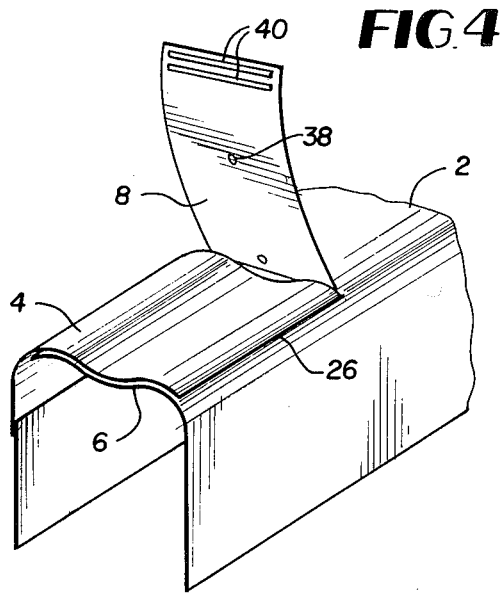
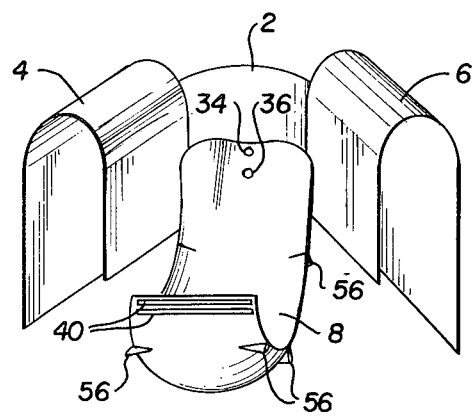
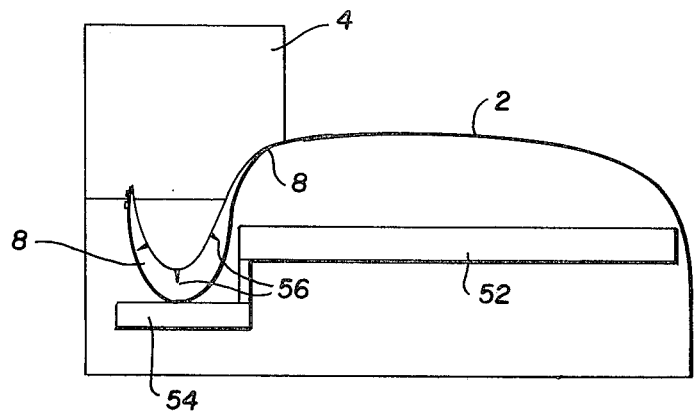

SURGICAL DRAPE

BACKGROUND OF THE INVENTION

This invention relates to a surgical drape which, although capable of different uses, is especially suited for procedures performed at or near the lower body.

Many surgical procedures are performed on the genital organs or require entry into the body through the lower body openings, i.e. the urinary, anal and genital orifices. Such procedures include cystoscopy examinations, bladder surgery, gynecological surgery and penile implant surgery.

Typically during such procedures, the patient is positioned on his or her back in a reclining position, with the legs either extended horizontally or held by stirrups in a raised divergent position, the latter being referred to as the lithotomy position. In the course of the procedure, body fluids are often released from the site of the procedure, such fluids comprising either natural excretions or injected fluids which are expelled by the patient. For example, a cystoscopy examination involves the insertion of an optical instrument through the urethera into the bladder for visual examination of these internal organs and, in some cases, collection of boty tissue specimens. Saline wash solutions or natural body excretions may be discharged in such procedures.

During lower body procedures, the patient is normally covered by a T-shaped drape which includes a main sheet of nonwoven fabrous material for covering the torso and a liquid impermeable longitudinal sheet which extends rearwardly from the main sheet to drape between the patient's legs. The longitudinal sheet has an access opening and a drain opening. The access opening provides access to the site of the procedure, and the drain opening enables fluids received by the longitudinal sheet to drain therefrom. In a cystocopy, the drain opening is positioned over a fluid-receiving trough which extends rearwardly from the operating room table.

Leggings are commonly used to cover the legs of a patient undergoing a lower body procedure. The leggings may be separate items or they may be connected to the drape, an example of the latter being disclosed in U.S. Pat. No. 3,862,632 issued Jan. 28, 1975.

Among the many types of surgical drapes available, there are products in which the arm or leg of a patient is extended through an opening in an elastic sheet formed of thermoplastic rubber. The size of the opening is such that the elasticity of the material will form a seal around the projecting limb. In another drape, the underside of the area surrounding the surgical access opening is provided with a pressure sensitive adhesive for adhering the drape directly to the patient. This adhesive is initially covered by a peelable sheet of plastic coated release paper which obstructs the opening until the release paper is removed.

Although not a surgical drape per se, another prior device of interest is a large funnel which is formed of plastic film and is adapted to receive fluids expelled during surgical procedures. The funnel itself is supported by tie strings attached respectively to the physician and to the table, and the funnel outlet is connected to a drain tube.

Keeping the foregoing in mind, it is an object of the present invention to provide a surgical drape which is quite versatile in the respect that it may be used for a variety of surgical procedures. Another object is to provide a surgical drape with leggings in an uncomplicated and effective manner. Another object is to provide a simple and effective means for preventing fluids from flowing over the margins of a fluid-receiving sheet of a surgical drape. A further object is to provide a surgical drape wherein the fluid-receiving sheet is provided with means for attaching it to the physician so the sheet shields the physician somewhat and maintains an appropriate shape. Still another object is to provide a drape which has a second access opening in a liquid impervious sheet, yet which is also capable of receiving and supporting fluids when only one body access opening is utilized. A further object is to provide a drape with a fluid receiving sheet which may be used alternatively in procedures when drainage from the sheet is desired and when drainage from the sheet is to be avoided.

SUMMARY OF THE INVENTION

The invention involves several advantageous features which, although being useful independently of each other, are preferably utilized together in a single surgical drape.

One feature of the invention involves the construction and arrangement of leg-covering portions on a surgical drape. The drape has a main sheet for draping over the torso of a patient and two leg flaps which drape over the legs of a patient. The leg flaps extend laterally inwardly in opposite directions, each leg flap having a free forward edge which is movable with respect to the main sheet and a free distal edge which is movable with respect to the main sheet. These flaps are preferably in mutually overlapping relationship, and they are capable of covering the legs of reclining patients which have their knees either straight or bent and raised in the lithotomy position.

Another feature of the invention relates to a drape provided with a fluid-receiving sheet which is attached to the physician performing the medical procedure. According to this feature, a flexible liquid-impervious longitudinal sheet has its forward end connected to a main sheet which drapes over the torso of a patient. An opening in the longitudinal sheet provides access to the body of a patient, and the rear end of the longitudinal sheet is provided with attachment means for attaching it to a physician. Preferably the distance from the access opening to the attachment means is at least about forty inches, and the longitudinal sheet has a fluid drain opening which is spaced from the body access opening by a distance which is from about forty-five to seventy-five percent of the distance between the access opening and the attachment means.

Still another feature of the invention relates to an arrangement which prevents liquids from flowing over the longitudinal edges of a fluid impervious longitudinal sheet, the forward end of which is connected to a torso-covering main sheet. The longitudinal sheet has an opening providing access to the body of a patient and, importantly, there are means for forming at least one transverse tuck in each of the longitudinal margin portions of the longitudinal sheet. This elevates the margins above the central portion of the longitudinal sheet to prevent liquid from flowing over the margins. The tuck forming means is preferably an adhesive material located in the margins, such adhesive material being covered by a removable cover member until such time that a tuck is to be formed. It is also desirable to provide the longitudinal sheet with a fluid drain opening, and to provide a removable liquid-impervious cover over the fluid drain opening. The longitudinal sheet may have a second opening which is located rearwardly of the first opening to provide a second access to the lower body of a patient. The second opening may also be covered by a removable liquid impervious barrier. The longitudinal sheet may be formed of elastic material, and the size of the first opening may be such that male genitalia may be drawn therethrough so the elasticity of the sheet will provide a seal therearound.

In a more specific respect, the invention involves a drape which has a liquid impervious longitudinal sheet connected at its forward end to a torso-covering main sheet, the longitudinal sheet having an opening providing access to the lower body of a patient. The longitudinal sheet receives and supports liquids introduced thereon in the course of surgical procedures. The rear end of the longitudinal sheet is provided with means for attaching it to the torso of a physician. Along the longitudinally extending margin portions of the longitudinal sheet, there are means for providing transverse tucks which elevate the margin portions above the central portion of the longitudinal sheet to prevent liquid from flowing over the margins. Further, the drape is provided with a pair of leg flaps for draping over the legs of a patient. These leg flaps lie rearwardly of the forward portion of the longitudinal sheet and they are arranged to extend laterally inwardly in opposite directions. Each leg flap has forward and distal edges which are movable with respect to the main sheet so that the leg flaps may cover the legs of a reclining patient, either with knees straight or with knees raised and bent in a lithotomy position.

According to another feature of the invention, a surgical drape has a main sheet for draping over the body of a patient and a liquid-impervious longitudinal sheet which is connected to the main sheet and is used to receive and support liquids introduced thereon in the course of surgical procedures. The longitudinal sheet has two openings which are spaced apart. One opening provides a first access to the body of a patient for the conduct of a surgical procedure, and the second opening provides a second access to the body of a patient. A removable liquid impervious barrier is positioned over the second opening to prevent fluid from flowing therethrough in procedures which do not require a second access to the patient's body. When such access is required, the barrier member is removed.

In accordance with still another feature of the invention, a removable liquid impervious barrier is provided over a drain opening in the longitudinal sheet. More specifically, the surgical drape has a main sheet for draping over the body of a patient and a liquid-impervious longitudinal sheet which is connected to the main sheet for receiving and supporting liquids introduced thereon in the course of surgical procedures. The longitudinal sheet has two openings which are spaced apart. One opening provides an access to the body of a patient for the conduct of a surgical procedure, and the second opening provides for the drainage of fluid from the sheet. A removable liquid impervious barrier is positioned over the drain opening to prevent from flowing therethrough in procedures where such drainage is not desired. When drainage is required, the barrier member is removed.

The various features described in this summary, although capable of independent use in a variety of drapes, are preferably used together in a surgical drape, an exemplary and preferred embodiment of which is shown in the drawings and described below.

BRIEF DESCRIPTION OF THE DRAWINGS

FIG. 3 is a sectional view taken through an aperture in the longitudinal sheet, showing a removable covering used in connection with access and/or drain openings in the drape.

FIG. 4 is a diagrammatic perspective view of the leg flap portion of the drape, showing its disposition when the drape is applied to a reclining patient whose knees are maintained in a straight condition.

FIG. 5 is a diagrammatic view showing the disposition of the leg flaps of the drape when it is applied to a reclining patient whose knees are raised and bent in a lithotomy position.

FIG. 6 is a diagrammatic cross sectional view of the drape when positioned as shown in FIG. 5.

DESCRIPTION OF A PREFERRED EMBODIMENT

Figure 1:
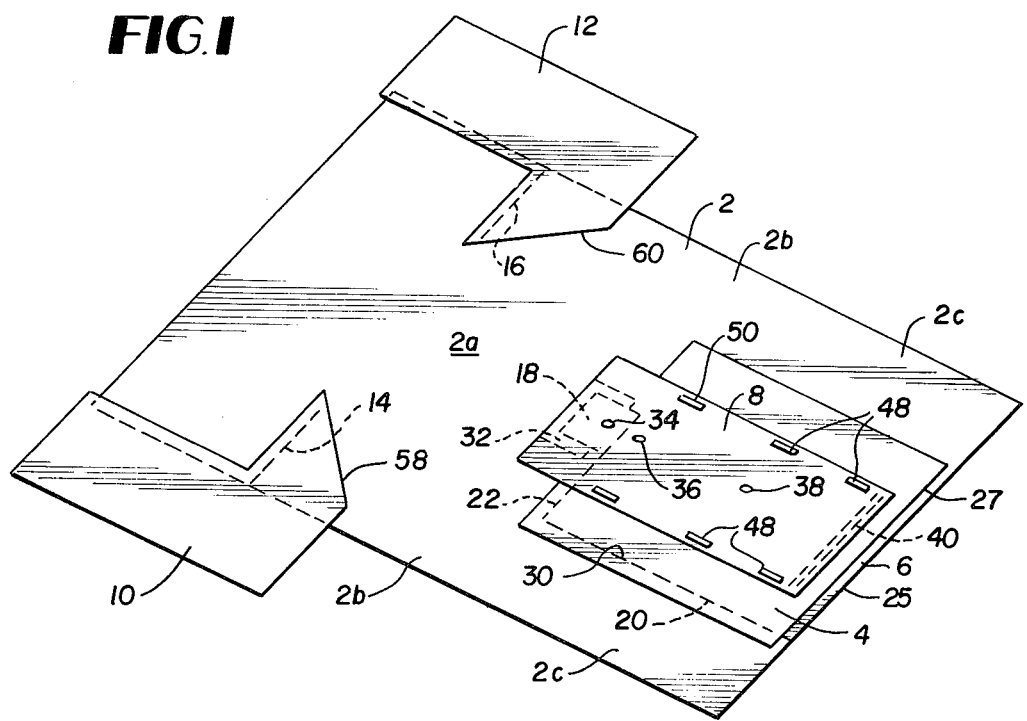
FIG. 1 is an isometric view of a surgical drape constructed in accordance with the invention.

The principal components of the surgical drape shown in FIG. 1 are a main sheet 2, for draping over at least the abdominal portion of the patient's torso, a pair of mutually overlapping leg flaps 4 and 6 for draping over the patient's legs, and a longitudinal T section sheet 8 for extending between the patient's legs where it will receive and support liquids which flow onto it in the course of surgical procedures. There are also a pair of wings 10 and 12 which provide gussets in the sides of the drape, thereby making it suitable for use in procedures where the patient's arms are in an outstretched position.

The main sheet 2, the leg flaps 4 and 6, and the wings 10 and 12 are formed of a soft, water repellent cellulosic material which has its tear resistance enhanced by a scrim or randomly oriented reinforcing filaments. One such material commonly used in the production of surgical drapes is sold under the trademark Kaycel by Kimberly-Clark Corporation, Neenah, Wis.

The longitudinal sheet 8 is made of a thin, highly flaccid, liquid impervious material. It is elastic so that any openings formed therein are enlargeable by stretching and will return to their initial size when released. As will be explained subsequently, this elasticity provides a sealing function which is particularly useful when the device is used in procedures involving the male genital organs.

Sheet 8 is preferably made of a thermoplastic rubber composition identified by the trademark Krayton by its manufacturer, Shell Chemical Company, Houston, Tex. Sheets of such material are produced by and are available from USI Film Products Division of U.S. Industrial Chemical Company, Tyler, Tex., and from Clopay Corporation, Trenton, N.J.

The main sheet 2 is rectangular and it has a width of 77 inches. As FIG. 1 is an isometric view drawn to scale, the dimensions of the various components of the drape may be determined by measurement and calculation. The main sheet has two transverse slits 14 and 16 associated with the wings 10 and 12, a rectangular opening 18 which is positionable over the area of the patent's body where the surgical procedure is to be conducted, and an inverted L-shaped slit comprising a longitudinal portion 20 and a transverse portion 22 which extends to the rear edge of the rectangular opening 18. This L-shaped slit 20,22 forms the leg flap 6.

The other leg flap 4, rather than being cut from the main sheet 2, is a separate rectangular piece of material. It is connected to the main sheet only by an L-shaped pattern of adhesive material which is located to the left of the longitudinal slit 20 and forward of the transverse slit 22 as seen in FIG. 1. This adhesive pattern is coterminus with the edge of the longitudinal sheet 8.

Figure 2:
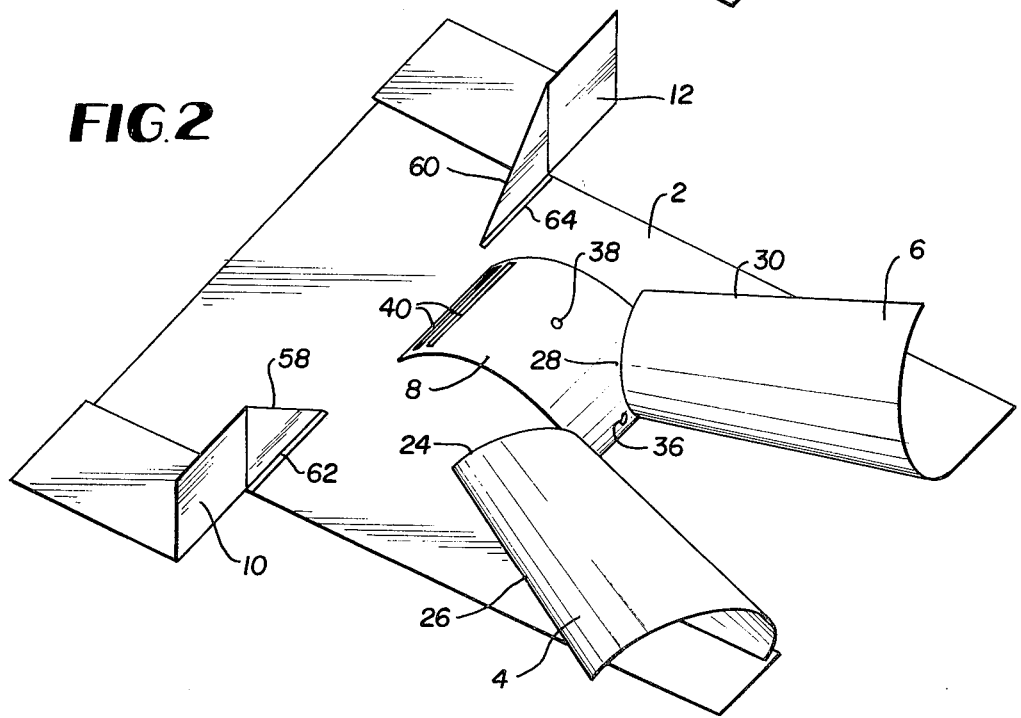
FIG. 2 is a view similar to FIG. 1, showing various elements thereof in raised positions to demonstrate the relationship between the drape components.

As seen in FIG. 1, the respective leg flap 4 is connected integrally to the main sheet 2, and the leg flap 6 is connected adhesively to the main sheet. They extend laterally inwardly in opposite directions. In FIG. 2 which shows the legs flaps 4 and 6 in raised positions, it will be seen that the flap 4 has a forward edge 24 and a distal edge 26 which are movable relative to the main sheet. Similarly, leg flap 6 has a forward edge 28 and a distal edge 30 which are movable relative to the main sheet. The respective leg flaps also have rear edges 25 and 27. Each of the forward edges 24 and 28, and each of the rear edges 25 and 27 is straight and unconnected to itself in order to permit the alternative uses of the drape as described below in connection with FIGS. 4 and 5. In this context, it will be noted that the term "distal" is used in a geometric sense to express the relationship relative to the connected longitudinal edge of the respective leg flap.

From the foregoing and from the drawings, it will be seen that the main sheet has a central portion 2a which drapes over the torso of a patient, and two side portions 2b which are on opposite sides of the central portion 2a where they are outboard of a patient covered by the drape. Extending rearwardly from the side portions 2b, there are a pair of spaced apart longitudinal extensions 2c. These extensions 2c are coplanar with the side portions 2b of the main sheet, where they will lie outboard of the patient's legs. The leg flaps 4 and 6 are connected to these extensions 2c, and they extend laterally inwardly in opposite directions in order to overlie the patient's legs. Also, as shown in FIGS. 4 and 5, the forward edges of the flaps 4 and 6 are movable to permit access to the lower body of a patient.

The longitudinal sheet 8 overlies the overlapping leg flaps 4 and 6 when, as shown in FIG. 1, the leg flaps are located in the same plane as the central portion 2a of the main sheet 2. Its forward portion is adhesively connected to the main sheet throughout its area which is forward of the leg flaps 4 and 6. To assure this adhesive connection, an intermediate U-shaped sheet which occupies the area 32 may be used. This U-shaped intermediate sheet in area 32, denoted a frame, has a lower cellulosic surface glued to the main sheet 2, and a thermoplastic upper surface which is heat sealed to the elastic material of the sheet 8.

In the longitudinally extending central portion of sheet 8 there are three openings 34, 36 and 38, each having a diameter of about one inch. The first and forwardmost opening 34 provides access to the lower body of a patient. Its size is such that a male penis, testicles and scrotum may be drawn therethrough and the elasticity of the sheet 8 will provide a seal which deters the flow of fluid through the opening. The second opening 36 provides a second access to the lower body of the patient. It is spaced about five inches from the first opening 34, this space being appropriate for situations where the principal opening 34 is used for access to the genital organs and the second opening 36 is used for access to the patient's rectal opening.

The third opening 38 is a fluid drain opening for discharging fluids from the sheet 8. It is preferably located from about 45% to about 75% of the distance from the primary opening 34 to the physicians attachment tapes 40 described below. This drain opening 38 is normally utilized in connection with cystocopy tables which are discussed later in this specification.

Inasmuch as the second access opening 36 and the drain opening 38 will not be used in connection with certain procedures, the upper or lower surface of the sheet 8 is normally provided with removable liquid impervious coverings which provide a barrier over the openings. The details of one such covering is shown in FIG. 3. This covering is a plastic coated piece of release paper 42 which is adhered to and peelable from a piece of tape 44 which has both of its faces provided with a pressure sensitive adhesive. The transfer tape 44 has an opening which is coextensive with the respective opening in sheet 8, and its lower surface is permanently adhered to the sheet 8. A corner of the transfer tape has been removed so that the paper 42 extends beyond the adhesive. This provides a tab 46 which may be grasped between the fingers for convenient removal of the barrier sheet 42.

At the rear end of the longitudinal sheet 8, on the lower surface thereof, there are two transfer tapes 40 which are used to attach the sheet 8 to the torso of a physician, particularly when the drape is being used in the manner shown in FIGS. 5 and 6 described below. These transfer tapes are preferably located at least about forty inches from the principal opening 34. They each have one adhesive surface permanently adhered to the sheet 8. The opposite adhesive surface is pressure sensitive and it is covered by a release paper which is peelable therefrom. The release paper extends laterally beyond the adhesive to provide a graspable tab which facilitates removal of the release paper. After the paper has been removed, the exposed adhesive may then be pressed against and adhered to the chest of the physician's gown.

As shown in FIG. 1, pressure sensitive adhesive tapes 48 are located along the margins of the sheet 8. These tapes are used to form tucks in the marginal portions of the sheet 8. As described below in connection with FIGS. 5 and 6, the tucks so formed will foreshorten the margins, thereby elevating the margins above the respective central portions of sheet 8 to deter the flow of liquid over the margins. These tapes 48 are initially covered by removable strips of release paper, one of which is shown at 50. Each of these protective strips 50 extends longitudinally beyond its respective adhesive area so that it may be easily grasped for removal. Strips 50 are not removed until the time that tucks are to be formed in the sheet 8.

One desirable feature of the invention is that the leg flaps are capable of covering the legs of patients who are reclined in different positions. In FIG. 4, for example, the leg flaps are disposed to cover the legs of a prone patient whose knees are straight. In the vicinity of the lower body of the patient, the leg flaps are folded between the legs to provide access to the lower body area as shown. Prior to the surgical procedure, the sheet 8, shown elevated for illustrative purposes, is laid down between the legs of the patient. Access to the patient is then provided through the first opening 34, and fluids are received on and retained by the upper surface of the impervious sheet 8.

Alternatively, the patient may be placed in the lithotomy position, with the knees raised and bent, the lower legs normally being held in an elevated horizontal position by stirrups. In this position the leg flaps 4 and 6 will be disposed as shown in FIGS. 5 and 6, each flap being reversely bent upon itself to receive and cover one leg of the patient. In this configuration, supplemental tapes or towel clamps may be used to hold the edges of the leg flaps together in a leg-enclosing position.

By way of background, it has been common for a physician, when performing a procedure on a patient in the lithotomy position, to be seated on a stool at the rear end of the table. The table is often provided with a rearwardly protruding cystocopy trough. Fluids from the patient flow downwardly across a liquid impervious longitudinal sheet into the cystocopy trough.

The practices described in the preceding paragraph may also be followed when using the surgical drape of the present invention. However, unlike the prior art surgical drapes, the sheet 8 is provided with tucks as described above, and it has a length and attachment means which enable it to be attached to the physician's torso. This disposition is best shown in FIG. 6 where the table is designated 52 and the cystocopy trough is shown at 54. The drain opening 38 of sheet 8 is located so fluids will drain into the trough 54. It will also be noted that the margins of the sheet have tucks 56 which effectively foreshorten the margins, elevating them above the central portion of sheet 8. This causes liquid to flow preferentially along the central portion of the sheet, and it prevents the liquid from flowing over the margins of the sheet 8. These tucks are made simply by removing the release papers 50 and folding each piece of adhesive tape 48 back upon itself.

In the course of using the drape, the drape is initially laid over a patient who is on the table in the lithotomy position. The leg flaps 4 and 6 are draped in inverted U-shaped configuration over the legs as shown in FIG. 5. Towel clamps or tapes may be applied to the front and rear edges of the leg flaps to enclose the legs fully. The cover 42 is removed from the drain opening 38. After the physician occupies his seated position at the rear end of the table, the release papers are removed from the attachment tapes 40 and the rear end of the impervious sheet 8 is adhered to his chest. At this point in time, the sheet 8 has the configuration shown in FIGS. 5 and 6.

If the procedure involves the male genitalia, the penis, testicles and scrotum are withdrawn through the opening 34. This enlarges the opening 34, but the elasticity of the sheet 8 causes it to constrict and form a seal therearound. If access to the rectum is appropriate, the covering 42 for opening 36 is removed to provide such access.

The wings 10 and 12 are known and they comprise no part of the present invention. They are L-shaped pieces of material which, as shown in FIGS. 1 and 2, are folded at 58 and 60 to form gussets. Flaps 62 and 64 on the underfolded part of the wings are adhesively bonded to the main sheet 2 along the rearward side of the respective slits 14 and 16. Forwardly of the slits 14 and 16, the wings are bonded to the longitudinal margins of the main sheet 2 and to the transverse areas 66 and 68 which are immediately forward of the slits 14 and 16.

Certain other components are preferably added to the illustrated drape. For example, it is desirable to provide the upper surface of the drape with a thin sheet of soft, open cell plastic foam which will prevent instruments from slipping off the drape. Such a sheet may be glued to the main sheet 2 in the area which overlies the patient's torso. Conventional tube holders for receiving surgical tubing may be bonded to the foam material. Also, it is desirable to provide retaining tapes which hold the rear edges of the leg flaps in the positions shown in FIG. 1 during shipping and initial handling at the hospital. These retaining tapes may be perforated for convenient separation which frees the flaps for movement to the positions occupied in surgical procedures.

Persons familiar with the field of the invention will recognize that the drape may take many forms other than the single embodiment disclosed hereinabove. Therefore, it is emphasized that the invention is not limited solely to the disclosed embodiment but is embracing of a wide variety of devices which adopt one or more of its significant features which fall within the spirit of the following claims.

I claim:

1. A surgical drape for use in connection with the performance of surgical procedures on the lower body of a patient, comprising,
    a main sheet for draping over the torso of a patient,
    a longitudinal sheet for extending between the legs of a patient, said longitudinal sheet having a forward portion connected to the main sheet and having an opening which provides access to the lower body of a patient for the conduct of a surgical procedure, said longitudinal sheet being formed of a material which is impervious to liquids so as to receive and support liquids introduced thereon in the course of surgical procedures, said longitudinal sheet having a rear end portion provided with attachment means for attaching it to the torso of a physician,
    said longitudinal sheet having a longitudinally extending central portion and longitudinally extending margin portions which lie on opposite sides of said central portion, means for forming at least one transverse tuck in each of said margin portions to elevate the margin portions above the central portion and prevent liquid on the longitudinal sheet from flowing over said margin portions,
    two leg flaps for draping over the legs of a patient, said leg flaps being connected to the main sheet and extending laterally inwardly in opposite directions in an area which is rearward on the drape with respect to said forward portion of the longitudinal sheet, each of said leg flaps having a forward edge which is movable with respect to the main sheet, and a distal edge which is movable with respect to the main sheet, said leg flaps being capable of covering the legs of a reclining patient with knees straight, said leg flaps also being capable of covering the legs of a reclining patient with knees raised and bent in a lithotomy position.

2. A surgical drape for use in connection with the performance of surgical procedures on the lower body of a patient, comprising,
    a main sheet, said main sheet having a central portion means for draping over the torso of a patient and two side portions which lie outboard of a patient, when covered by the drape, said side portions lying on opposite sides of the central portion means, a pair of spaced apart longitudinal extensions which extend rearwardly from said side portions so as to lie outboard of the legs of a patient, and extend coplanar within the side portions of the main sheet, two leg flap means for draping over the legs of a patient, said leg flap means being connected to the longitudinal extensions and extending laterally inwardly in opposite directions to overlie the legs of a patient, each of said leg flap means having a free forward edge means, a free rear edge and a free distal edge, said free forward edge means being vertically movable at locations which lie forwardly of said central portion means of the main sheet to permit access to the lower body of a patient and to permit movement of the leg flap means to positions corresponding to the positions of the legs of a patient covered by the drape, a longitudinal sheet means for draping between the patient's legs extending from the rear of said central portion means of the main sheet, said longitudinal sheet means overlying the leg flap means when the leg flap means are horizontally flat and lie entirely in the same plane of the said central portion means of the main sheet.

3. A surgical drape according to claim 2 wherein said leg flap means are in mutually overlapping relationship.

4. A surgical drape according to claim 2 wherein each of said leg flap means is reversely bent upon itself so as to receive the leg of a patient therebeneath.

5. A surgical drape according to claim 2, said longitudinal sheet means having an opening which provides access to the lower body of a patient for the conduct of a surgical procedure, said longitudinal sheet means being formed of a material which is impervious to liquids so as to receive and support liquids introduced thereon in the course of surgical procedures.

6. A surgical drape according to claim 5 wherein said longitudinal sheet means has a rear end portion provided with attachment means for attaching it to the torso of a physician.

7. A surgical drape according to claim 5 wherein said longitudinal sheet means has a longitudinally extending central portion and longitudinally extending margin portions which lie on opposite sides of said central portion, means for forming at least one transverse tuck in each of said margin portions to foreshorten the margin portions and elevate them above the central portion to prevent liquid on the longitudinal sheet means from flowing over said margin portions.

8. A surgical drape for use in connection with the performance of surgical procedures on a patient, comprising, a main sheet for draping over the torso of a patient, a longitudinal sheet, said longitudinal sheet having a forward portion connected to the main sheet and having a first opening which provides access to the body of a patient for the conduct of a surgical procedure, said longitudinal sheet being formed of a material which is impervious to liquids so as to receive and support liquids introduced thereon in the course of surgical procedures, said longitudinal sheet having a longitudinally extending central portion and longitudinally extending margin portions which lie on opposite sides of said central portion, means for forming at least one transverse tuck means in each of said margin portions to foreshorten the margin portions and elevate them above the central portion of the sheet to prevent liquid on the longitudinal sheet from flowing over said margin portions.

9. A surgical drape according to claim 8 wherein the means for forming transverse tucks means is an adhesive material located in said margin portions.

10. A surgical drape according to any one of claims 8 or 9 wherein said longitudinal sheet has a rear end portion provided with attachment means for attaching it to the torso of a physician.

11. A surgical drape according to claim 10 wherein the distance from the first opening to the attachment means for attaching the longitudinal sheet to the torso of a physician is at least about 40 inches.

12. A surgical drape according to claim 10 wherein the longitudinal sheet has a fluid drain opening spaced from the first opening by a distance which is about 45 to 75 percent of the distance between the first opening and the attachment means.

13. A surgical drape according to claim 12 having a removable liquid impervious covering positioned over said fluid drain opening, said liquid impervious covering being separably attached to the longitudinal sheet and being arranged so that removal of said covering will permit the drainage of fluid through said fluid drain opening.

14. A surgical drape according to claim 8 or 9 having a second opening located rearwardly of said first opening, said second opening providing a second access to the lower body of a patient, and a removable liquid impervious barrier positioned over said second opening, said liquid impervious covering being separably attached to the longitudinal sheet and being arranged so that removal of said covering will permit the access to the lower body of a patient through said second opening.

15. A surgical drape according to claim 8 or 9 wherein the longitudinal sheet has a fluid drain opening located between its forward end portion and its rear end portion.

16. A surgical drape according to claim 15 having a removable liquid impervious covering positioned over said fluid drain opening, said liquid impervious covering being separably attached to the longitudinal sheet and being arranged so that removal of said covering will permit the drainage of fluid through said fluid drain opening.

17. A surgical drape for use in connection with the performance of surgical procedures on the body of a patient, comprising, a main sheet for draping over the torso of a patient, said main sheet having a central portion means for draping over the torso of a patient and two side portions which lie outboard of a patient, when covered by the drape, said side portions lying on opposite sides of the central portion means, a longitudinal sheet having a forward portion connected to the main sheet and having a first opening which provides access o the body of a patient for the conduct of a surgical procedure, said longitudinal sheet means being formed of a material which is impervious to liquids so as to receive and support liquids introduced thereon in the course of surgical procedures, said longitudinal sheet means having a second body access opening means which is spaced from said first opening to provide a second access to the lower body of the patient, and a removable liquid impervious covering positioned over said second opening means to prevent the flow of fluid through said second opening means in procedures which do not require said second access to the patient's body, said liquid impervious covering being separably attached to the longitudinal sheet and being arranged so that removal of said covering will permit the access to the lower body of a patient through said second opening means for procedures which require said second access to the patient's body.

18. A surgical drape for use in connection with the performance of surgical procedures on the body of a patient, comprising, a main sheet for draping over the torso of a patient, said main sheet having a central portion means for draping over the torso of a patient and two side portions which lie outboard of a patient, when covered by the drape, said side portions lying on opposite sides of the central portion means, a longitudinal sheet means having a forward portion connected to the main sheet and having a first opening which provides access to the body of a patient for the conduct of a surgical procedure, said longitudinal sheet being formed of a material which is impervious to liquids so as to receive and support liquids introduced thereon in the course of surgical procedures, said longitudinal sheet also having a preformed fluid drain opening means which is spaced from the first opening to provide for drainage of fluid from the longitudinal sheet, and a removable liquid impervious covering positioned over said fluid drain opening means to prevent the drainage of fluid through the longitudinal sheet in procedures which do not involve such drainage, said liquid impervious covering being separably attached to the longitudinal sheet and being arranged so that removal of said covering will permit the drainage of fluid through said fluid drain opening means for procedures which involve such drainage.

19. A surgical drape for use in connection with the performance of surgical procedures on a patient, comprising, a main sheet for draping over the torso of a patient, a longitudinal sheet, said longitudinal sheet having a forward portion connected to the main sheet and having a first opening which provides access to the body of a patient for the conduct of a surgical procedure, said longitudinal sheet being formed of a material which is impervious to liquids so as to receive and support liquids introduced thereon in the course of surgical procedures, said longitudinal sheet having a longitudinally extending central portion and longitudinally extending margin portions which lie on opposite sides of said central portion, means for forming at least one transverse tuck in each of said margin portions to foreshorten the margin portions and elevate them above the central portion to prevent liquid on the longitudinal sheet from flowing over said margin portions, said means for forming transverse tucks is an adhesive material located in said margin portions, and a removable member for covering said adhesive material until such time that a tuck is to be formed in the longitudinal sheet.

20. A surgical drape according to claim 19 wherein said longitudinal sheet has a rear end portion provided with attachment means for attaching it to the torso of a physician.

21. A surgical drape according to claim 20 wherein the distance from the first opening to the attachment means for attaching the longitudinal sheet to the torso of a physician is at least about 40 inches.

22. A surgical drape according to claim 20 wherein the longitudinal sheet has a fluid drain opening spaced from the first opening by a distance which is about 45 to 75 percent of the distance between the first opening and the attachment means.

23. A surgical drape according to claim 22 having a removable liquid impervious covering positioned over said fluid drain opening.

24. A surgical drape according to claim 19 having a second opening located rearwardly of said first opening, said second opening providing a second access to the lower body of a patient, and a removable liquid impervious barrier positioned over said second opening.

25. A surgical drape according to claim 19 wherein the longitudinal sheet is formed of elastic material, said first opening having a size such that male genitalia may be drawn therethrough and the elasticity of the sheet material will provide a seal therearound.

26. A surgical drape according to claim 19 wherein the longitudinal sheet has a fluid drain opening located between its forward end portion and its rear end portion.

27. A surgical drape according to claim 26 having a removable liquid impervious covering positioned over said fluid drain opening.

28. A surgical drape for use in connection with the performance of surgical procedures on a patient, comprising, a main sheet for draping over the torso of a patient, a longitudinal sheet, said longitudinal sheet having a forward portion connected to the main sheet and having a first opening which provides access to the body of a patient for the conduct of a surgical procedure, said longitudinal sheet being formed of a material which is impervious to liquids so as to receive and support liquids introduced thereon in the course of surgical procedures, said longitudinal sheet being formed of elastic material, said first opening having a size such that male genetalia may be drawn therethrough and the elasticity of the sheet material will provide a seal therearound, said longitudinal sheet having a longitudinally extending central portion and longitudinally extending margin portions which lie on opposite sides of said central portion, means for forming at least one transverse tuck in each of said margin portions to elevate the margin portions above the central portion and prevent liquid on the longitudinal sheet from flowing over said margin portions.

29. A surgical drape according to claim 28 wherein the means for forming transverse tucks is an adhesive material located in said margin portions.

30. A surgical drape according to claim 29 including a removable member for covering said adhesive material until such time that a tuck is to be formed in the longitudinal sheet.

31. A surgical drape for use in connection with the performance of surgical procedures on a patient, comprising, a main sheet for draping over the torso of a patient,
a longitudinal sheet having a forward portion connected to the main sheet and having a first opening which provides access to the body of a patient for the conduct of a surgical procedure, said longitudinal sheet being formed of a flexible material which is impervious to liquids so as to receive and support liquids introduced thereon in the course of surgical procedures, said longitudinal sheet having a rear end portion provided with attachment means for attaching it to a physician,
said longitudinal sheet being formed of elastic material, said first opening having a size such that male genitalia may be drawn therethrough and the elasticity of the sheet material will provide a seal therearound.

32. A surgical drape according to claim 31 wherein the distance from the first opening to the attachment means for attaching the longitudinal sheet to the torso of a physician is at least about 40 inches.

33. A surgical drape according to claim 31 wherein the longitudinal sheet has a fluid drain opening spaced from the first opening by a distance which is about 45 to 75 percent of the distance between the first opening and the attachment means.

* * * * *